United States Patent
Dean et al.

(10) Patent No.: US 7,045,524 B2
(45) Date of Patent: May 16, 2006

(54) PLEUROMUTILIN DERIVATIVES WITH ANTIMICROBIAL ACTIVITY

(75) Inventors: David Kenneth Dean, Harlow (GB); Antoinette Naylor, Harlow (GB); Andrew Kenneth Takle, Harlow (GB)

(73) Assignee: SmithKline Beecham p.l.c., Middlesex (GB)

( * ) Notice: Subject to any disclaimer, the term of this patent is extended or adjusted under 35 U.S.C. 154(b) by 172 days.

(21) Appl. No.: 10/416,432

(22) PCT Filed: Nov. 12, 2001

(86) PCT No.: PCT/GB01/04995

§ 371 (c)(1),
(2), (4) Date: Oct. 17, 2003

(87) PCT Pub. No.: WO02/38528

PCT Pub. Date: May 16, 2002

(65) Prior Publication Data

US 2005/0143393 A1    Jun. 30, 2005

(30) Foreign Application Priority Data

Nov. 11, 2000    (GB) ................ 0027705.3

(51) Int. Cl.
*A61K 31/495* (2006.01)
*A61K 31/439* (2006.01)
*C07D 295/185* (2006.01)
*C07D 453/02* (2006.01)
*C07C 69/38* (2006.01)

(52) U.S. Cl. ............ 514/255.01; 514/305; 514/511; 544/391; 546/133; 560/117; 560/173; 560/194

(58) Field of Classification Search ............ 560/117, 560/173; 544/391; 514/255.01, 511
See application file for complete search history.

(56) References Cited

FOREIGN PATENT DOCUMENTS

WO    WO 99/21855    5/1999

*Primary Examiner*—Emily Bernhardt
(74) *Attorney, Agent, or Firm*—Linda E. Hall; Stephen A. Venetianer; Charles M. Kinzig

(57) ABSTRACT

Pleuromutilin compounds of the formula:

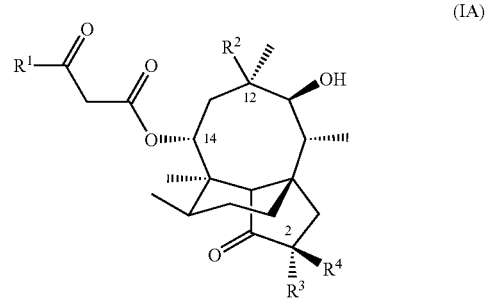

(IA)

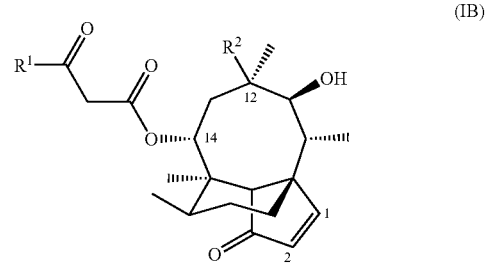

(IB)

are of use in anti-bacterial therapy.

12 Claims, No Drawings

PLEUROMUTILIN DERIVATIVES WITH ANTIMICROBIAL ACTIVITY

The present invention relates to novel compounds, to processes for their preparation, to pharmaceutical compositions containing them and to their use in medical therapy, particularly antibacterial therapy.

Pleuromutilin, the compound of formula (A), is a naturally occurring antibiotic which has antimycoplasmal activity and modest antibacterial activity. Mutilin and other compounds with a free OH at C-14 are inactive. The impact of further modification at C-14 on the activity of pleuromutilin has been investigated (H. Egger and H. Reinshagen, J. Antibiotics, 1976, 29, 923). Replacing the hydroxy group of the glycolic ester moiety at position 14 by another O, S or N-linked group was found to improve anti-microbial activity. Thus, introducing a diethylaminoethylthio group gives the compound of formula (B), also known as Tiamulin, which is used as a veterinary antibiotic (G. Hogenauer in Antibiotics, Vol. V, part 1, ed. F. E. Hahn, Springer-Verlag, 1979, p. 344).

In this application, the non-conventional numbering system which is generally used in the literature (G. Hogenauer, loc. cit.) is used.

WO 97/25309 (SmithKline Beecham) describes further modification of the acyloxy group, disclosing 14-O-carbamoyl derivatives of mutilin or 19,20-dihydromutilin, in which the N-atom of the carbamoyl group is unsubstituted, mono- or di-substituted.

WO98/05659 (SmithKline Beecham) discloses 14-O-carbamoyl derivatives of mutilin or 19,20-dihydromutilin, in which the N-atom of the carbamoyl group is acylated by a group which includes an azabicyclic moiety.

WO 99/21855 (SmithKline Beecham) describes further derivatives of mutlin or 19,20-dihydromutilin, in which the glycolic ester moiety at position 14 is replaced by the group $R^2(CH_2)_mX(CH_2)_nCH_2COO-$ in which $R^2$ is a non-aromatic mono- or bicyclic group.

WO 00/27790 (SmithKline Beecham) describes C-14 spirocyclic, acylcarbamate, heteroaryalkyl carboxylate or arylalkoxyalkyl carboxylate derivatives of mutilin or 19,20-dihydromutilin.

WO 00/37074 (SmithKline Beecham) describes further derivatives of mutilin or 19,20-dihydromutilin having a heteroaryl acetate substituent at the C-14 position.

WO 00/73287 (SmithKline Beecham) describes further derivatives of mutilin or 19,20-dihydromutilin having an isoxazoline carboxylate substituent at the C-14 position.

WO 01/14310 (SmithKline Beecham) describes further derivatives of mutilin or 19,20-dihydromutilin having a β-ketoester substituent at the C-14 position.

In addition, 19,20-dihydro-2α-hydroxy-mutilin is described by G. Schulz and H. Berner in Tetrahedron, 1984, vol. 40, pp 905–917, and a number of C-14 ether, carbamate, amide and urea derivatives of mutilin or 19,20-dihydromutilin are described by Brooks et al. in Bioorg. Med. Chem, 2001, vol. 9, pp 1221–1231.

The present invention is based on the unexpected discovery that novel mutilin derivatives having a malonamide or malonic ester substituent at the 14-position also have potent antimicrobial activity.

Accordingly the present invention provides a compound of formula (IA) or (IB):

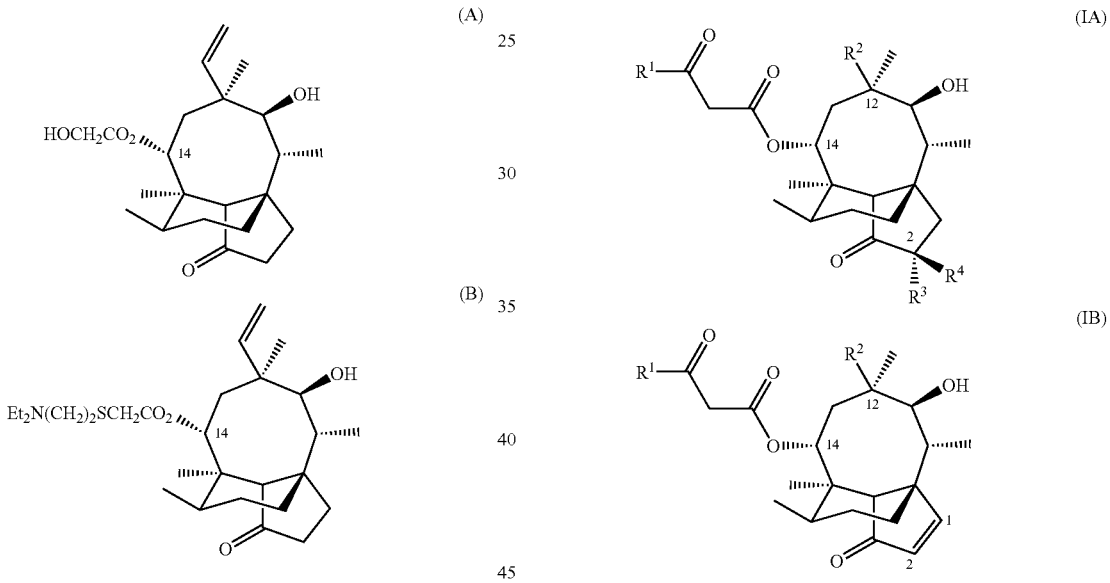

in which:
$R^1$ is $OR^5$ or $NR^6R^7$;
$R^2$ is vinyl or ethyl;
$R^3$ is H, OH or F; and $R^4$ is H; or $R^3$ is H and $R^4$ is F;
in which:
$R^5$ is hydrogen or optionally substituted ($C_{1-6}$) alkyl; and
either:
$R^6$ is hydrogen, ($C_{1-4}$)alkyl or optionally substituted aryl; and
$R^7$ is aminoalkyl, a nitrogen containing heterocycle, or an optionally substituted aryl ($C_{1-4}$)alkyl group; or
$R^6$ and $R^7$, together with the nitrogen atom to which they are attached, form an optionally substituted piperazine ring.

Representative examples of substituents for a piperazine ring include aryl, for example phenyl; ($C_{1-6}$)alkyl, for example methyl; and aryl($C_{1-4}$)alkyl, for example benzyl.

When $R^7$ is aryl($C_{1-4}$)alkyl, it is preferably benzyl.

Representative examples of $R^5$ include ($C_{1-6}$)alkyl, for example methyl.

Representative examples of $R^1$ when $NR^6R^7$ is a piperazine ring include 4-substituted piperazine, e.g. 4-methylpiperazine, 4-benzyl piperazine and 4-phenylpiperazine.

Representative values for $R^6$ and $R^7$ are not joined to form a piperazine ring include hydrogen.

Representative values for $R^1$ include methoxy, 4-methoxybenzylamino, 4-phenylpiperazinyl, 2-dimethylaminoethylamino, 4-methylpiperazinyl, 4-benzylpiperazinyl and 1-azabicyclo[2.2.2]oct-3-ylamino.

When used herein the term "aminoalkyl" refers to, unless otherwise defined, a mono- or di-$(C_{1-6})$alkylamino-$(C_{1-6})$alkyl group. When $R^7$ is aminoalkyl, representative aminoalkyl groups include di-$(C_{1-6})$alkylamino-$(C_{1-6})$alkyl, preferred aminoalkyl groups include 2-dimethylaminoethyl.

When used herein the term "nitrogen containing heterocycle" refers to a saturated or partially saturated non-aromatic mono- or bicyclic group linked via a ring carbon atom. The group may comprise one to three nitrogen atoms, preferably one or two, more preferably one nitrogen atom. When the group is monocyclic it can contain between 4 and 8 ring atoms, and when bicyclic it can contain between 5 and 10 ring atoms in each ring. The azabicyclic ring system may, for example, be represented by the formulae (X) or (Y):

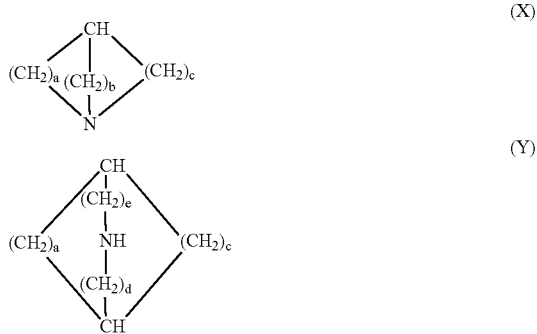

wherein each of a, b, c, d and e, which may be the same or different, is for a, b and c an integer from 1 to 4, and for d and e 0 or an integer from 1 to 3, such that any one ring has between 5 and 10 ring atoms.

The linking ring carbon in an azabicyclic system may be a bridgehead atom or a non-bridgehead atom.

The nitrogen containing heterocycle can be optionally substituted on carbon by up to 3 substituents. Suitable substituents include $(C_{1-6})$alkyl, $(C_{1-6})$alkyloxy, $(C_{2-6})$alkenyl and $(C_{2-6})$alkenyloxy, each of which may be carried by either a bridgehead or a non-bridgehead carbon atom. In addition, the or each nitrogen atom may be substituted by oxygen, to form an N-oxide, or by mono- or di-$(C_{1-6})$alkyl, in which case it will be appreciated that a quaternary cation can be formed. Representative nitrogen substituents include $(C_{1-6})$alkyl, preferably methyl. The counterion may be a halide ion such as chloride or bromide, preferably chloride. The ring system additionally may contain one or more double bonds.

Representative examples of $R^7$ when a nitrogen containing heterocycle include optionally substituted azabicyclooctyl. Preferred nitrogen containing heterocyclic moieties include optionally substituted 1-azabicyclo[2.2.2]oct-3-yl.

When used herein, the term "aryl" refers to, unless otherwise defined, phenyl or naphthyl. A substituted aryl group comprises up to five, preferably up to three substituents.

Suitable substituents for an aryl group, including phenyl when forming part of a benzyl group, include, for example, and unless otherwise defined, halogen, $(C_{1-6})$alkyl, aryl, aryl$(C_{1-6})$alkyl, $(C_{1-6})$alkoxy, $(C_{1-6})$alkoxy$(C_{1-6})$alkyl, halo $(C_{1-6})$alkyl, aryl$(C_{1-6})$alkoxy, hydroxy, nitro, cyano, azido, amino, mono- and di-N-$(C_{1-6})$alkylamino, acylamino, arylcarbonylamino, acyloxy, carboxy, carboxy salts, carboxy esters, carbamoyl, mono- and di-N-$(C_{1-6})$alkylcarbamoyl, $(C_{1-6})$alkoxycarbonyl, aryloxycarbonyl, ureido, guanidino, $(C_{1-6})$alkylguanidino, amidino, $(C_{1-6})$alkylamidino, sulphonylamino, aminosulphonyl, $(C_{1-6})$alkylthio, $(C_{1-6})$alkylsulphinyl, $(C_{1-6})$alkylsulphonyl, heterocyclyl, heteroaryl, heterocyclyl$(C_{1-6})$alkyl and heteroaryl$(C_{1-6})$alkyl. In addition, two adjacent ring carbon atoms may be linked by a $(C_{3-5})$ alkylene chain, to form a carbocyclic ring.

Representative aryl substituents include $(C_{1-6})$alkoxy, e.g. methoxy.

When used herein, the terms "alkyl" and "alkenyl" refer to (individually or as part of alkoxy or alkenyloxy) straight and branched groups containing up to six carbon atoms.

When used herein, the terms "cycloalkyl" and "cycloalkenyl" refer to groups having from three to eight ring carbon atoms.

When substituted, an alkyl, alkenyl, cycloalkyl or cycloalkenyl group may comprise up to four substituents, preferably up to two substituents. Suitable substituents for alkyl, alkenyl, cycloalkyl or cycloalkenyl groups include aryl, heteroaryl, heterocyclyl, $(C_{1-6})$alkoxy, $(C_{1-6})$alkylthio, aryl$(C_{1-6})$alkoxy, aryl$(C_{1-6})$alkylthio, amino, mono- or di-$(C_{1-6})$alkylamino, cycloalkyl, cycloalkenyl, carboxy and esters thereof, amide, ureido, guanidino, $(C_{1-6})$alkylguanidino, amidino, $(C_{1-6})$alkylamidino, $(C_{1-6})$acyloxy, azido, hydroxy, and halogen.

When used herein the terms "heterocyclyl" and "heterocyclic" refer to, unless otherwise defined, non-aromatic, single and fused, rings suitably containing up to four heteroatoms in each ring, each of which is selected from oxygen, nitrogen and sulphur. Each heterocyclic ring preferably has from 4 to 7, preferably 5 or 6, ring atoms. A fused heterocyclic ring system may include carbocyclic rings and need include only one heterocyclic ring.

When substituted, a heterocyclyl group may comprise up to three substituents. Preferably a substituent for a heterocyclyl group is selected from oxo, and the group hereinbefore defined as suitable aryl substituents.

When used herein, the term "heteroaryl" suitably includes, unless otherwise defined, a mono- or bicyclic heteroaromatic ring system comprising up to four, preferably 1 or 2, heteroatoms each selected from oxygen, nitrogen and sulphur. Each ring may have from 4 to 7, preferably 5 or 6, ring atoms. A bicyclic heteroaromatic ring system may include a carbocyclic ring.

When substituted, a heteroaryl group may comprise up to three substituents. Preferably a substituent for a heteroaryl group is selected from the group hereinbefore defined as suitable aryl substituents.

Depending on the substituents, two or more diastereoisomers may be possible. In that situation the present invention includes the individual diastereoisomers and mixtures thereof.

The 2-hydroxy-substituted compounds of formula (IA) are of the (2S) configuration. The 2-F-substituted compounds of formula (IA) may of (2S) configuration or (2R) configuration, or be provided as mixtures thereof. The (2S) configuration is however preferred.

Representative compounds of the invention include:

Mutilin 14-[methyl malonate];

Mutilin 14-[N-(4-methoxybenzyl)malonamate];

Mutilin 14-[3-(4-phenylpiperazin-1-yl)-3-oxo-propionate];

Mutilin 14-[N-(2-dimethylaminoethyl)malonamate];

Mutilin 14-[3-(4-methylpiperazin-1-yl)-3-oxo-propionate];

Mutilin 14-[3-(4-benzylpiperazin-1-yl)-3-oxo-propionate]; and

Mutilin 14-{N-[3(RS)-1-azabicyclo{2.2.2}oct-3-yl]malonamate.

Preferred compounds of the invention include:

Mutilin 14-[3-(4-phenylpiperazin-1-yl)-3-oxo-propionate];

Mutilin 14-[3-(4-methylpiperazin-1-yl)-3-oxo-propionate];

Mutilin 14-[3-(4-benzylpiperazin-1-yl)-3-oxo-propionate]; and

Mutilin 14-{N-[3(RS)-1-azabicyclo{2.2.2}oct-3-yl]malonamate.

The compounds of this invention may be in crystalline or non-crystalline form, and, if crystalline, may optionally be hydrated or solvated. This invention includes within its scope stoichiometric hydrates as well as compounds containing variable amounts of water.

The compounds according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight.

Compounds of the invention that contain a basic group such as an amino substituent may be in the form of a free base or an acid addition salt. Compounds having an acidic group such as a carboxy substituent may be in the form of a pharmaceutically acceptable salt. Compounds of the invention having both a basic and an acidic centre may be in the form of zwitterions, acid addition salt of the basic centre or alkali metal salts (of the carboxy group). Pharmaceutically acceptable salts are preferred.

Pharmaceutically acceptable acid-addition salts include those described by Berge, Bighley, and Monkhouse, *J. Pharm. Sci.,* 1977, 66, 1–19. Suitable salts include the hydrochloride, maleate, and methanesulphonate; particularly the hydrochloride.

Pharmaceutically acceptable salts include those described by Berge, Bighley, and Monkhouse, *J. Pharm. Sci.,* 1977, 66, 1–19. Suitable salts include alkali metal salts such as the sodium and potassium salts.

Compounds of the present invention may be readily prepared from a pleuromutilin or a 19,20-dihydro-pleuromutilin derivative by adapting procedures well known in the art for forming ester groups. Suitable procedures are reviewed in, for example, I. O. Sutherland in *Comprehensive Organic Chemistry*, Vol. 2, ed. I. O. Sutherland, p. 869, Pergamon, 1979; and J. M. Brown, ibid., p. 779.

Accordingly, the present invention provides a process for the preparation of a compound of formula (IA) or (IB) in which $R^1$ is $OR^5$ which comprises reacting a compound of formula (IIA) or (IIB):

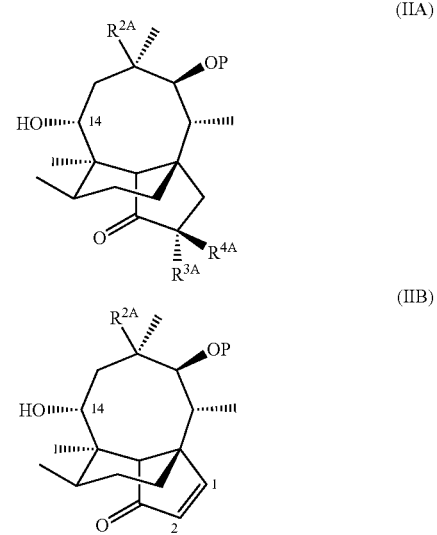

in which:

P is hydrogen or an hydroxy-protecting group;

$R^{2A}$, $R^{3A}$ and $R^{4A}$ are $R^2$, $R^3$ and $R^4$ as defined for formulae (IA) and (IB) or a group convertible to $R^2$, $R^3$ and $R^4$ respectively;

with a malonyl halide of formula (III):

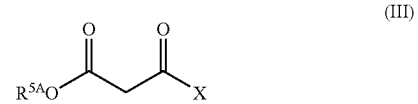

in which:

$R^{5A}$ is $R^5$ as defined for formulae (IA) and (IB) or a group convertible to $R^5$; and X is halogen;

under ester forming conditions and thereafter, and if so needed;

converting P to hydrogen, and if necessary converting an $R^{2A}$, $R^{3A}$, $R^{4A}$ or $R^{5A}$ group to an $R^2$, $R^3$, $R^4$ or $R^5$ group.

A representative halogen is chlorine.

Suitable ester forming conditions are known in the art (e.g. I. O. Sutherland in *Comprehensive Organic Chemistry*, Vol. 2, ed. I. O. Sutherland, p. 869, Pergamon, 1979 and J. Mulzer in *Comprehensive Organic Functional Group Transformation*, Vol. 5, ed. C. J. Moody, p. 121, Elsevier Scientific, Oxford, 1995). and include pre-treatment of the compound of formula (IIA) or (IIB) with a base such as sodium bis(trimethylsilyl)amide in a solvent such as tetrahydrofuran at −40° C. to −20° C. prior to treatment with a suitable acylating agent [e.g. compounds of formula (III)].

The present invention also provides a process for preparing a compound of formula (IA) or (IB) in which $R^1$ is $NR^6R^7$ which comprises reacting a compound of formula (IVA) or (IVB):

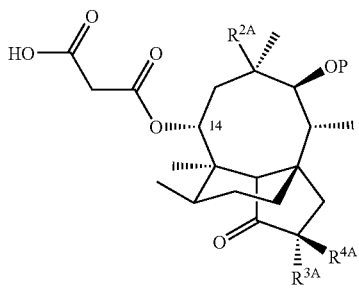

(IVA)

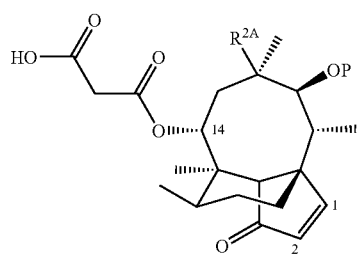

(IVB)

in which:
P is hydrogen or an hydroxy-protecting group; and
$R^{2A}$, $R^{3A}$ and $R^{4A}$ are as hereinbefore defined for formulae (IIA) and (IIB);
with a compound of formula (V):

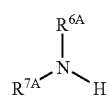

(V)

in which:
$R^{6A}$ and $R^{7A}$ are $R^6$ and $R^7$ as defined for formulae (IA) and (IB) or a group convertible to $R^6$ and $R^7$ respectively;
under amide forming conditions and thereafter, and if so needed;
converting P to hydrogen, and if necessary
converting an $R^{2A}$, $R^{3A}$, $R^{4A}$, $R^{6A}$ or $R^{7A}$ group to an $R^2$, $R^3$, $R^4$, $R^6$ or $R^7$ Suitable amide forming conditions are well known in the art (e.g P. D. Bailey, I. D. Collier and K. M. Morgan in *Comprehensive Organic Functional Group Transformation*, Vol. 5, ed. C. J. Moody, p. 257, Elsevier Scientific, Oxford, 1995) and include an organic solvent such as anhydrous dimethyl formamide or anhydrous ethyl acetate at a temperature of −10° C. to 50° C. (preferably −5° C. to 25° C.), in the presence of a dialkylcarbodiimide, e.g. 1,3-dicyclohexylcarbodiimide; or 1-(3-dimethylaminopropyl)-3-ethylcarbodiimide and hydroxybenzotriazole.

Conversion of an $R^{1A}$, $R^{2A}$, $R^{3A}$ or $R^{4A}$ group to an $R^1$, $R^2$, $R^3$ or $R^4$ group typically arises if a protecting group is needed during the above reactions or during the preparation of the reactants by the procedures described below.

When P is a hydroxyl protecting group, a preferred protecting group is acyl, for example so that —OP is trifluoroacetoxy or dichloroacetoxy. When the intended $R^3$ is also hydroxyl, then $R^{3A}$ is also preferably acyloxy, for example acetyl or dichloroacetyl. Hydroxyl groups at positions 11 and 2 (as groups OP and $R^{3A}$) may be protected using, for example, trifluoroacetic anhydride or dichloroacetic anhydride and pyridine in tetrahydrofuran or N-trifluoroacetyl-imidazole in tetrahydrofuran at 0° C. After either of the reactions described above with (III) or (V) is complete, the protecting acyl groups may be removed to restore the hydroxyl groups, for instance by hydrolysis e.g. using NaOH in either MeOH or tetrahydrofuran/water solution.

Suitable hydroxy, carboxy and amino protecting groups are those well known in the art and which may be removed under conventional conditions and without disrupting the remainder of the molecule. A comprehensive discussion of the ways in which hydroxy, carboxy and amino groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991). Particularly suitable hydroxy protecting groups include, for example, triorganosilyl groups such as, for instance, trialkylsilyl and also organocarbonyl and organooxycarbonyl groups such as, for instance, acetyl, allyloxycarbonyl and 4-methoxybenzyloxycarbonyl Particularly suitable carboxy protecting groups include alkyl and aryl esters, for instance methyl, ethyl and phenyl. Particularly suitable amino protecting groups include alkoxycarbonyl and 4-methoxybenzyloxycarbonyl.

$R^{2A}$ is typically the $R^2$ group vinyl, and this may be converted to the alternative $R^2$ ethyl group by hydrogenating the vinyl group to form an ethyl group, typically by hydrogenation over a palladium catalyst (e.g. 10% palladium-on-carbon) in a solvent such as ethyl acetate, ethanol, dioxane, or tetrahydrofuran.

$R^{3A}$ is typically hydrogen, fluoro or protected hydroxyl, such as acyloxy. After the coupling reaction, if required, protecting acyl groups may be removed to restore the hydroxyl groups by hydrolysis e.g. using NaOH in MeOH.

A compound of formula (IA) may also be prepared from an epi-mutilin starting material. Accordingly in a further aspect, the present invention provides a process for preparing a compound of formula (IA) in which $R^3$ and $R^4$ are both hydrogen and $R^1$ is $OR^5$ which comprises reacting an epi-mutilin compound of formula (IIC):

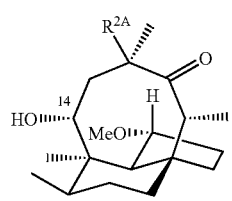

(IIC)

in which $R^{2A}$ is $R^2$ as defined for formulae (IA) and (IB), or a group convertible to $R^2$;
with a compound of formula (III) as hereinbefore defined;
to give a compound of formula (VI):

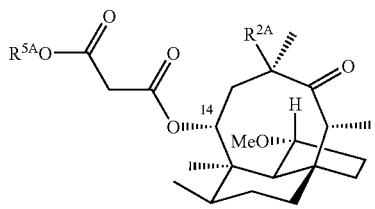

(VI)

and then treating the product with an acid;
and where required or desired converting an $OR^{5A}$ group to an $R^1$ group and an $R^{2A}$ group to an $R^2$ group.

In a yet further aspect, the present invention provides a process for preparing a compound of formula (IA) in which $R^3$ and $R^4$ are both hydrogen and $R^1$ is $NR^6R^7$ which comprises reacting an epi-mutilin compound of formula (IVC):

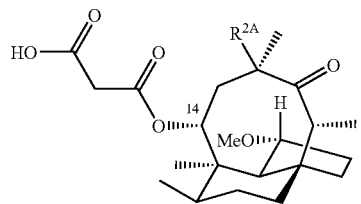

(IVC)

wherein $R^{2A}$ is as hereinbefore defined;
with a compound (V), as hereinbefore defined in an amide-forming reaction as hereinbefore described;
and then treating the product with an acid;
and where required or desired converting an $R^{2A}$ group to an $R^2$ group, an $R^{6A}$ group to an $R^6$ group and an $R^{7A}$ group to an $R^7$ group.

The acid treatment indicated above converts the epi-mutilin configuration to the usual mutilin nucleus of formula (IIA). Typically this conversion is carried out by treatment with conc. HCl or Lukas reagent (conc. HCl saturated with $ZnCl_2$) in dioxane.

It should be appreciated that it may be necessary to interconvert one $R^1$, $R^2$, $R^3$ or $R^4$ group to another $R^1$, $R^2$, $R^3$ or $R^4$ group. This typically arises when one compound of formula (IA/B) is used as the immediate precursor of another compound of formula (IA/B) or when it is easier to introduce a more complex or reactive substituent at the end of a synthetic sequence. A substituent group in $R^1$ can be converted into another substituent group using one of the general methods for functional group transformation described in the literature (e.g. a carboxylic ester can be hydrolysed to a carboxylic acid with base; an acid can be converted into an amide; a tert-butoxycarbonylamino group can be converted into an amine by treatment with trifluoroacetic acid; an amino group can be alkylated or acylated), provided that the method chosen is compatible with other functional groups in the molecule (e.g. the ketone at C-3 in the pleuromutilin nucleus).

Functional group transformations are well known in the art and are described in, for instance, *Comprehensive Organic Functional Group Transformations*, eds. A. R. Katritzky, O. Meth-Cohn, and C. W. Rees (Elsevier Science Ltd., Oxford, 1995), *Comprehensive Organic Chemistry*, eds. D. Barton and W. D. Ollis (Pergamon Press, Oxford, 1979), and *Comprehensive Organic Transformations*, R. C. Larock (VCH Publishers Inc., New York, 1989).

$R^{2A}$ is typically the $R^2$ group vinyl, and this may be converted to the alternative $R^2$ ethyl group by hydrogenating the vinyl group to form an ethyl group, typically by hydrogenation over a palladium catalyst (e.g. 10% palladium-on-carbon) in a solvent such as ethyl acetate, ethanol, dioxane, or tetrahydrofuran.

Compounds of formulae (IIA) in which $R^{3A}$ and $R^{4A}$ are hydrogen, (IIB) and (IIC) may be readily prepared according to methods described in the literature, for example G. Schulz and H. Berner, *Tetrahedron*, 1984, 40, 905, and in WO 97/25309 and WO 98/05659 (SmithKline Beecham). Where necessary, and as hereinbefore described, saponification of the C-14 ester may be carried out at an appropriate stage.

Compounds of formula (IIA) in which $R^{3A}$ is hydroxyl or fluoro may be prepared from pleuromutilin, via an intermediate 2-diazo compound, the preparation of which is described by G. Schulz and H. Berner in *Tetrahedron*, 1984, 40, 905. Where necessary, saponification of the C-14 ester group may be carried out at an appropriate stage using conventional techniques such as sodium hydroxide or sodium methoxide in methanol or aqueous tetrahydrofuran solution.

The intermediate 2-diazo compound may be reacted with a carboxylic acid to give a 2-acyloxy-mutilin derivative. Suitably, reaction with dichloroacetic acid gives a 2-dichloroacetoxy-mutilin derivative, which can be deprotected as described above to provide the (2S)-2-hydroxy derivative, at an appropriate stage.

Compounds of formula (IIA) in which $R^{3A}$ is fluoro may be obtained by reacting 2-diazo-mutilin with a source of hydrogen fluoride. Conveniently, the hydrogen fluoride source is an amine complex of hydrogen fluoride such as hydrogen fluoride-pyridine. The reaction may be carried out in an anhydrous solvent (e.g. diethyl ether, tetrahydrofuran, 1,2-dimethoxyethane), at a temperature of −15° C. to 25° C. This reaction produces (2S)-2-fluoro derivatives. (2R)-2-Fluoro-mutilin derivatives may be prepared by treating the (2S)-isomer with a base (e.g. sodium hydroxide or potassium hydroxide in ethanol). This will usually produce a mixture of (2S) and (2R)-isomers that may be separated using conventional techniques such as chromatography and crystallisation.

Compounds of formula (III) are available commercially.
Compounds of formula (IVC) may be prepared by hydrolysis of a compound of formula (VI). Compounds of formula (IVA) in which $R^{3A}$ and $R^{4A}$ are hydrogen may be prepared by treating an epi-mutilin compound of formula (VI) with acid to give a mutilin compound, followed by hydrolysis.

Compounds of formulae (IVA) and (IVB) may also be prepared from compounds of formulae (IA) or (IB) in which $R^1$ is $OR^5$ by saponification.

Compounds of formula (V) are available commercially, or may be readily prepared by adapting procedures well known in the art for preparing amines (e.g. C. M. Marson and A. D. Hobson, *Comprehensive Organic Functional Group Transformation*, Vol. 2, ed. S. V. Ley, p. 297, Elsevier Scientific, Oxford, 1995).

The compounds of the present invention may contain a chiral centre, and therefore the above processes may produce a mixture of diastereoisomers. A single diastereoisomer may be prepared by separating such a mixture of diastereoisomers by conventional techniques such as chromatography or fractional crystallisation.

The compounds of this invention may be in crystalline or non-crystalline form, and, if crystalline, may optionally be hydrated or solvated. When some of the compounds of this invention are allowed to crystallise or are recrystallised from organic solvents, solvent of crystallisation may be present in the crystalline product. Similarly, some of the compounds of this invention may be crystallised or recrystallised from solvents containing water. In such cases water of hydration may be present in the crystalline product. Crystallisation procedures will usually produce stoichiometric hydrates. Compounds containing variable amounts of water may be produced by processes such as lyophilisation.

The compounds according to the invention are suitably provided in substantially pure form, for example at least 50% pure, suitable at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

The present invention also includes pharmaceutically acceptable salts and derivatives of the compounds of the invention. Salt formation may be possible when one of the substituents carries an acidic or basic group. Salts may be prepared by salt exchange in conventional manner.

Acid-addition salts may be pharmaceutically acceptable or non-pharmaceutically acceptable. In the latter case, such salts may be useful for isolation and purification of the compound of the invention, or intermediates thereto, and will subsequently be converted into a pharmaceutically acceptable salt or the free base.

The compounds of the present invention and their pharmaceutically acceptable salts or derivatives have antimicrobial properties and are therefore of use in therapy, in particular for treating microbial infections in animals, especially mammals, including humans, in particular humans and domesticated animals (including farm animals). The compounds may be used for the treatment of infections caused by, for example, Gram-positive and Gram-negative bacteria and mycoplasmas, including, for example, *Staphylococcus aureus, Staphylococcus epidermidis, Enterococcus faecalis, Streptococcus pyogenes, Streptococcus agalactiae, Streptococcus pneumoniae, Haemophilus* sp., *Neisseria* sp., *Legionella* sp., *Chlamydia* sp., *Moraxella catarrhalis, Mycoplasma pneumoniae,* and *Mycoplasma gallisepticum.*

The present invention also provides a method of treating microbial infections in animals, especially in humans and in domesticated mammals, which comprises administering a compound of the invention or a pharmaceutically acceptable salt or derivative or solvate thereof, or a composition according to the invention, to a patient in need thereof.

The invention further provides the use of a compound of the invention or a pharmaceutically acceptable salt or derivative or solvate thereof in the preparation of a medicament for use in the treatment of microbial infections.

Compounds of the present invention may be used to treat skin and soft tissue infections and acne, by topical application. Accordingly, in a further aspect the present invention provides the use of a compound of the invention or a pharmaceutically acceptable salt or derivative or solvate thereof in the preparation of a medicament adapted for topical administration for use in the treatment of skin and soft tissue infections and also in the treatment of acne in humans.

Compounds of the present invention may be also used for the elimination or reduction of nasal carriage of pathogenic bacteria such as *S. aureus, H. influenzae, S. pneumonia* and *M. catarrhalis*, in particular colonisation of the nasopharynx by such organisms, by the administration of a compound of the present invention thereto. Accordingly, in a further aspect, the present invention provides for the use of a compound of the invention or a pharmaceutically acceptable salt or derivative or solvate thereof in the manufacture of a medicament adapted for administration to the nasal cavity, for reducing or eliminating the nasal carriage of pathogenic organisms. Preferably, the medicament is adapted for focussed delivery to the nasopharynx, in particular the anterior nasopharynx.

Such reduction or elimination of nasal carriage is believed to be useful in prophylaxis of recurrent acute bacterial sinusitis or recurrent otitis media in humans, in particular in reducing the number of episodes experienced by a patient over a given period of time or increasing the time intervals between episodes. Accordingly, in a further aspect, the present invention provides for the use of a compound of the invention or a pharmaceutically acceptable salt or derivative or solvate thereof in the manufacture of a medicament adapted for administration to the nasal cavity, for prophylaxis of recurrent acute bacterial sinusitis or recurrent otitis media.

Compounds of the present invention are also useful in treating chronic sinusitis. Accordingly, in a further aspect, the present invention provides for the use of a compound of the invention or a pharmaceutically acceptable salt or derivative or solvate thereof in the manufacture of a medicament, for treating of chronic sinusitis.

The compounds according to the invention may suitably be administered to the patient at a daily dosage of from 1.0 to 50 mg/kg of body weight. For an adult human (of approximately 70 kg body weight), from 50 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

To lessen the risk of encouraging the development of resistant organisms during prophylaxis of recurrent otitis media or recurrent acute bacterial sinusitis, it is preferred to administer the drug on an intermittent, rather than a continual, basis. In a suitable intermittent treatment regimen for prophylaxis of recurrent otitis media or recurrent sinusitis, drug substance is administered on a daily basis, for a small number of days, for instance from 2 to 10, suitably 3 to 8, more suitably about 5 days, the administration then being repeated after an interval, for instance, on a monthly basis over a period of months, for instance up to six months. Less preferably, the drug substance may be administered on a continuing, daily basis, over a prolonged period, for instance several months. Suitably, for prophylaxis of recurrent otitis media or recurrent sinusitis, drug substance is administered once or twice a day. Suitably, drug substance is administered during the winter months when bacterial infections such as recurrent otitis media and recurrent sinusitis tend to be more prevalent. The drug substance may be administered at a dosage of from 0.05 to 1.00 mg, typically about 0.1 to 0.2 mg, in each nostril, once or twice a day.

More generally, the compounds and compositions according to the invention may be formulated for administration in any convenient way for use in human or veterinary medicine, by analogy with other antibiotics.

Accordingly, in a further aspect, the present invention provides a pharmaceutical composition comprising a compound of the invention or a pharmaceutically acceptable salt or derivative or solvate thereof together with a pharmaceutically acceptable carrier or excipient.

The compounds and compositions according to the invention may be formulated for administration by any route, for example oral, topical or parenteral. The compositions may, for example, be made up in the form of tablets, capsules, powders, granules, lozenges, creams, syrups, sprays or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, nose drops, nasal sprays, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, ethanol or oleyl alcohol for lotions and aqueous bases for sprays. Such carriers may constitute from about 1% to about 98% by weight of the formulation; more usually they will constitute up to about 80% by weight of the formulation.

Compositions according to the invention intended for topical administration, in addition to the above, may also contain a steroidal anti-inflammatory agent; for example, betamethasone.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilised before being filled into a suitable vial or ampoule, which is then sealed. Advantageously, conventional additives including, for example, local anaesthetics, preservatives, and buffering agents can be dissolved in the vehicle. In order to enhance the stability of the solution, the composition may be frozen after being filled into the vial, and the water removed under vacuum; the resulting dry lyophilised powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

A compound or composition according to the invention is suitably administered to the patient in an antimicrobially effective amount.

A composition according to the invention may suitably contain from 0.001% by weight, preferably (for other than spray compositions) from 10 to 60% by weight, of a compound according to the invention (based on the total weight of the composition), depending on the method of administration.

When the compositions according to the invention are presented in unit dosage form, for instance as a tablet, each unit dose may suitably comprise from 25 to 1000 mg, preferable from 50 to 500 mg, of a compound according to the invention.

Representative compositions of the present invention include those adapted for intranasal administration, in particular, those that will reach into the nasopharynx. Such compositions are preferably adapted for focussed delivery to, and residence within, the nasopharynx. The term 'focussed delivery' is used to mean that the composition is delivered to the nasopharynx, rather than remaining within the nares. The term 'residence' within the nasopharynx is used to mean that the composition, once delivered to the nasopharynx, remains within the nasopharynx over a course of several hours, rather than being washed away more or less immediately. Preferred compositions include spray compositions and creams. Representative spray compositions include aqueous compositions, as well as oily compositions that contain amphiphilic agents so that the composition increases in viscosity when in contact with moisture. Creams may also be used, especially creams having a rheology that allows the cream to spread readily in the nasopharynx.

Preferred aqueous spray compositions include, in addition to water, further excipients including a tonicity modifier such as a salt, for instance sodium chloride; preservative, such as benzalkonium salt; a surfactant such as a non-ionic surfactant, for instance a polysorbate; and buffer, such as sodium dihydrogen phosphate; present in low levels, typically less than 1%.

The pH of the composition may also be adjusted, for optimum stability of the drug substance during storage. For compounds of the present invention, a pH in the range 5 to 6, preferably about 5.3 to 5.8, typically about 5.5 is optimal.

Representative oily spray and cream compositions are described in WO 98/14189 (SmithKline Beecham). Representative aqueous sprays are described in International Application no PCT/GB98/03211 (SmithKline Beecham).

Suitably, the drug substance is present in compositions for nasal delivery in between 0.001 and 5%, preferably 0.005 and 3%, by weight of the composition. Suitable amounts include 0.5% and 1% by weight of the composition (for oily compositions and creams) and from 0.01 to 0.2% (aqueous compositions).

Spray compositions according to the present invention may be delivered to the nasal cavity by spray devices well known in the art for nasal sprays, for instance an air lift pump. Preferred devices include those that are metered to provide a unit volume of composition, preferably about 100 μl, and optionally adapted for nasal administration by addition of a modified nozzle.

The invention is illustrated by the following Examples.

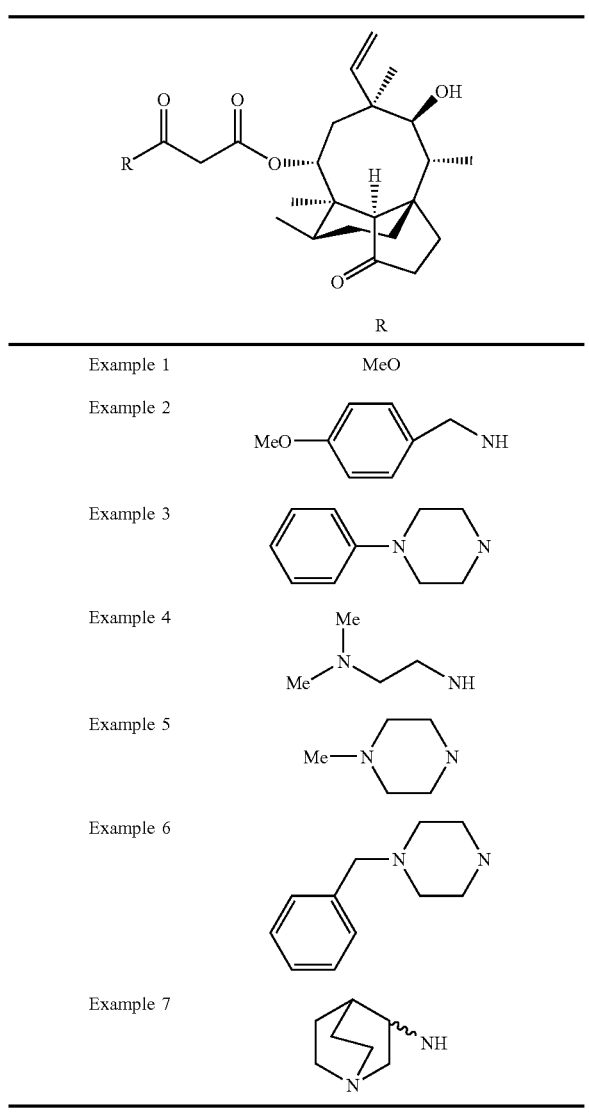

| | R |
|---|---|
| Example 1 | MeO |
| Example 2 | MeO—⟨phenyl⟩—CH₂—NH |
| Example 3 | ⟨phenyl⟩—N⟨piperazine⟩N |
| Example 4 | Me—N(Me)—CH₂CH₂—NH |
| Example 5 | Me—N⟨piperazine⟩N |
| Example 6 | ⟨benzyl⟩—N⟨piperazine⟩N |
| Example 7 | ⟨bicyclic amine⟩—NH |

EXAMPLE 1

Mutilin-14-(methyl malonate)

Step 1. (3R)-3-Deoxo-11-deoxy-3-methoxy-11-oxo-4-epi-mutilin 14-(methyl malonate)—A solution of (3R)-3-deoxo-11-deoxy-3-methoxy-11-oxo-4-epi-mutilin {H. Berner et al, Tetrahedron, 1980, 36, 1807} (5.0 g, 15.0 mmol) in dry tetrahydrofuran (75 ml) was cooled to −30° C., treated with sodium bis(trimethylsilyl)amide (15 ml, 1.0M solution in tetrahydrofuran, 15.0 mmol) and stirred for 5 minutes. Methyl malonyl chloride (2.36 ml, 22.5 mmol) in dry tetrahydrofuran was added dropwise to the solution. The mixture was stirred at −30° C. for 30 minutes, warmed to room temperature and stirred for a further 16 hours. The reaction was quenched with aqueous ammonium chloride solution and the product extracted into ethyl acetate, washed with water and brine and dried ($Na_2SO_4$). The product was purified by chromatography on silica gel eluting with 5% ethyl acetate in hexane. The title compound was isolated as a colourless oil (5.0 g, 77%); MS(Electrospray) m/z 433 [M−H]⁻.

Step 2. Mutilin-14-(methyl malonate)—The product of Step 1 (2.0 g, 4.6 mmol) in dioxane (5 ml) was treated with a saturated solution of zinc chloride in conc. HCl (10 ml) and the reaction stirred at room temperature for 1.5 hours. The solution was poured into ethyl acetate and saturated aqueous sodium hydrogen carbonate solution. The aqueous phase was re-extracted with ethyl acetate and the combined organic phases were washed with brine. The organic phase was dried ($MgSO_4$) and purified by chromatography on silica gel eluting with 20% ethyl acetate in hexane. The title compound was isolated as a yellow oil (520 mg, 27%); MS(Electrospray) m/z 419 [M−H]⁻.

EXAMPLE 2

Mutilin 14-[N-(4-methoxybenzyl)malonamate]

Step 1. (3R)-3-Deoxo-11-deoxy-3-methoxy-11-oxo-4-epi-mutilin 14-malonate—A solution of the product of Example 1 Step 1 (1.8 g, 4.1 mmol) in dry tetrahydrofuran (70 ml) was treated with sodium hydroxide (340 mg, 8.5 mmol) in water (30 ml) and stirred for 18 hours. The solution was washed with diethyl ether, acidified with 2M hydrochloric acid and the product extracted into dichloromethane and dried ($Na_2SO_4$). The title compound was isolated as a colourless foam (1.49 g, 86%); ¹H NMR ($CDCl_3$) inter alia 0.82 (3H, d, J 6.8 Hz), 1.00 (3H, d, J 6.4 Hz), 2.49 (1H, dd, J 15.3, 10.0 Hz), 2.89 (1H, q, J 6.3 Hz), 3.23 (3H, s), 3.40 (2H,s), 3.46 (1H, m), 5.02 (1H, d, J 17.5 Hz), 5.31 (1H, d, J 10.7 Hz), 5.82 (1H, d, J9.9Hz), 6.61 (1H, dd, J 17.5, 10.7 Hz).

Step 2. (3R)-3-Deoxo-11-deoxy-3-methoxy-11-oxo-4-epi-mutilin 14-[N-(4-methoxybenzyl)malonamate]—A solution of 4-methoxybenzylamine (0.035 ml, 0.24 mmol) in dry DMF (3 ml) was added dropwise to a mixture of the product of Step 1 (100 mg, 0.24 mmol), hydroxybenzotriazole (75 mg, 0.53 mmol) and 1-(3-dimethylaminopropyl)-3-ethylcarbodiimide (57 mg, 0.26 mmol) in dry DMF (5 ml) at 0° C. The mixture was allowed to warm to room temperature and stirred for 18 hours. The mixture was concentrated and the residue dissolved in ethyl acetate. The organic solution was washed with 0.5M hydrochloric acid (×2), dilute aqueous sodium hydrogen carbonate solution (×3), brine and dried ($Na_2SO_4$). The title compound was isolated as a colourless foam (110 mg, 86%); MS(Electrospray) m/z 538 [M−H]⁻.

Step 3. Mutilin-14-[N-(4-methoxybenzyl)malonamate]— The product of Step 2 (100 mg, 0.19 mmol) in dioxane (3 ml) was treated with a saturated solution of zinc chloride in conc. HCl (3 ml) and the reaction stirred at room temperature for 3 hours. The solution was poured into ethyl acetate and saturated aqueous sodium hydrogen carbonate solution. The aqueous phase was re-extracted with ethyl acetate and the combined organic phases were washed with brine. The organic phase was dried (MgSO$_4$) and purified by chromatography on silica gel eluting with 2% (9:1 methanol: ammonia (35%)) in dichloromethane. The title compound was isolated as a colourless foam (55 mg, 56%); MS(Electrospray) m/z 524 [M−H]$^-$.

EXAMPLE 3

Mutilin 14-[3-(4-phenylpiperazin-1-yl)-3-oxo-propionate]

Step 1. (3R)-3-Deoxo-11-deoxy-3-methoxy-11-oxo-4-epi-mutilin 14-[3-(4-phenylpiperazin-1-yl)-3-oxo-propionate]—A solution of the product of Example 2, Step 1 (200 mg, 0.48 mmol) and 1-phenylpiperazine (77 mg, 0.48 mmol) in dry ethyl acetate (5 ml) was cooled to 0° C. and treated with 1,3-dicyclohexylcarbodiimide (114 mg, 0.58 mmol) in ethyl acetate. The solution was stirred at 0° C. for 3 hours, warmed to room temperature and stirred for 18 hours. The resulting suspension was filtered and the solution concentrated. The title compound was isolated as a colourless foam (220 mg, 82%); MS(Electrospray) m/z 565 [M+H]$^+$.

Step 2. Mutilin-14-[3-(4-phenylpiperazin-1-yl)-3-oxo-propionate—The product of Step 1 (100 mg, 0.19 mmol) in dioxane (3 ml) was treated with concentrated HCl (3 ml) and the reaction stirred at room temperature for 3 hours. The solution was poured into ethyl acetate and saturated aqueous sodium hydrogen carbonate solution. The aqueous phase was re-extracted with ethyl acetate and the combined organic phases were washed with brine. The organic phase was dried (MgSO$_4$), concentrated and the product triturated with diethyl ether. The title compound was isolated as a colourless solid (97 mg, 47%); MS(Electrospray) m/z 551 [M+H]$^+$.

The following examples were prepared by the general two-step method described in Example 3.

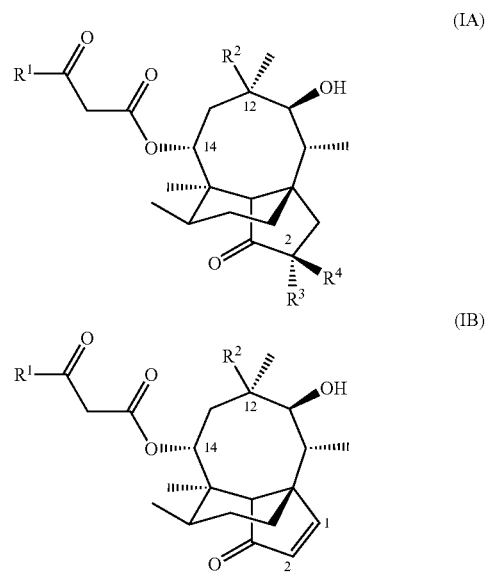

in which:
$R^1$ is OR$^5$ or NR$^6$R$^7$;
$R^2$ is vinyl or ethyl;
$R^3$ is H, OH or F; and $R^4$ is H; or $R^3$ is H and $R^4$ is F;
in which:
$R^5$ is (C$_{1-6}$) alkyl; and
either:
$R^6$ is hydrogen, [(C$_{1-4}$)alkyl or optionally substituted aryl]; and
$R^7$ is aminoalkyl, azabicyclooctyl, or an aryl (C$_{1-4}$)alkyl group which may be substituted by C$_{1-6}$alkoxy; or
$R^6$ and $R^7$, together with the nitrogen atom to which they are attached, form a piperazine ring which may be substituted by aryl, C$_{1-6}$alkyl, or aryl(C$_{1-4}$alkyl);

| Example | Amine | Characterisation |
| --- | --- | --- |
| 4 Mutilin 14-[N-(2-dimethylaminoethyl)-malonamate] | N,N-Dimethylethylenediamine | MS(Electrospray) m/z 447 [M + H]$^+$ |
| 5 Mutilin 14-[3-(4-methylpiperazin-1-yl)-3-oxo-propionate] | 1-Methylpiperazine | MS(Electrospray) m/z 489 [M + H]$^+$ |
| 6 Mutilin 14-[3-(4-benzylpiperazin-1-yl)-3-oxo-propionate] | 1-Benzylpiperazine | MS(Electrospray) m/z 565 [M + H]$^+$ |
| 7 Mutilin 14-{N-[3(RS)-1-azabicyclo[2.2.2]oct-3-yl]malonamate} | 3(RS)-3-Amino-1-azabicyclo[2.2.2]octane | MS(Electrospray) m/z 515 [M + H]$^+$ |

Biological Data

Compounds of the present invention were assessed for anti-bacterial activity in a conventional MIC assay against a range of pathogenic organisms.

Compounds were found to have MICs in the range 0.06 to 4 μg/ml against *Staph aureus* Oxford and 0.06 to 64 μg/ml against *Strep pneumoniae* (R6).

The invention claimed is:

1. A compound of Formula (IA) or (IB):

or a pharmaceutically acceptable salt thereof.

2. A compound according to claim 1 in which R$^1$ is NR$^6$R$^7$, and R$^6$ is hydrogen.

3. A compound according to claim 1 in which R$^1$ is NR$^6$R$^7$, and R$^7$ is aryl(C$_{1-4}$)alkyl which may be substituted by C$_{1-6}$alkoxy.

4. A compound according to claim 1 in which R$^1$ is NR$^6$R$^7$, and R$^6$ and R$^7$, together with the nitrogen atom to which they are attached, form a piperazine ring which may be substituted by aryl, (C$_{1-6}$)alkyl or aryl(C$_{1-4}$)alkyl.

5. A compound according to claim 1 in which R$^1$ is OR$^5$, and R$^5$ is (C$_{1-6}$)alkyl.

6. A compound according to claim 1 in which $R^1$ is methoxy, 4-methoxybenzylamino, 4-phenylpiperazinyl, 2-dimethylaminoethylamino, 4-methylpiperazinyl, 4-benzylpiperazinyl or 1-azabicyclo[2.2.2]oct-3-ylamino.

7. A compound according to claim 1 selected from:
Mutilin 14-[methyl malonate];
Mutilin 14-[N-(4-methoxybenzyl)malonamate];
Mutilin 14-[3-(4-phenylpiperazin-1-yl)-3-oxo-propionate];
Mutilin 14-[N-(2-dimethylaminoethyl)malonamate];
Mutilin 14-[3-(4-methylpiperazin-1-yl)-3-oxo-propionate];
Mutilin 14-[3-(4-benzylpiperazin-1-yl)-3-oxo-propionate]; and
Mutilin 14-{N-[3(RS)-1-azabicyclo{2.2.2}oct-3-yl]malonamate.

8. A pharmaceutical composition comprising a compound according to claim 1, and a pharmaceutically acceptable carrier.

9. A method of treating microbial infections in animals, especially in humans and in domesticated mammals, which comprises administering a compound according to claim 1, to a patient in need thereof.

10. A method of treating or preventing recurrent otitis media or recurrent sinusitis in humans, which comprises nasally administering a compound according to claim 1, to a patient in need thereof.

11. A method of treatment of skin and soft tissue infections and in the treatment of acne in humans, which comprises topically administering a compound according to claim 1, to a patient in need thereof.

12. A process for preparing a compound of formula (IA) or (IB) as claimed in claim 1 which process comprises:

(a) for a compound of formula (IA) or (IB) in which $R^1$ is $OR^5$, reacting a compound of formula (IIA) or (IB):

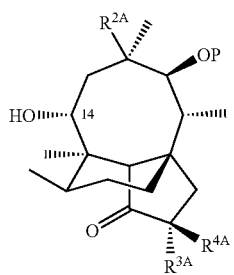
(IIA)

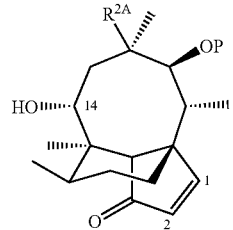
(IIB)

in which:
P is hydrogen or an hydroxy-protecting group;
$R^{2A}$, $R^{3A}$ and $R^{4A}$ are $R^2$, $R^3$ and $R^4$ as defined for formulae (IA) and (IB) or a group convertible to $R^2$, $R^3$ and $R^4$ respectively;
with a malonyl halide of formula (III):

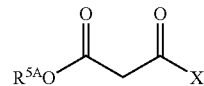
(III)

in which:
$R^{5A}$ is $R^5$ as defined for formulae (IA) and (IB) or a group convertible to $R^5$; and
X is halogen;
under ester forming conditions and thereafter, and if so needed;
converting P to hydrogen, and if necessary
converting an $R^{2A}$, $R^{3A}$, $R^{4A}$ or $R^{5A}$ group to an $R^2$, $R^3$, $R^4$ or $R^5$ group;

(b) for a compound of formula (IA) or (IB) in which $R^1$ is $NR^6R^7$, reacting a compound of formula (IVA) or (IVB):

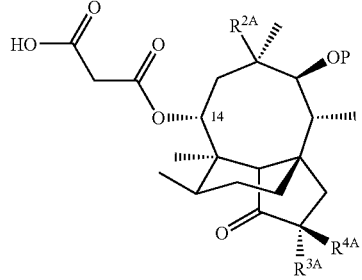
(IVA)

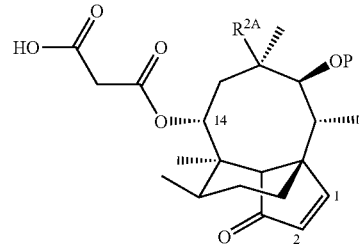
(IVB)

in which:
P is hydrogen or an hydroxy-protecting group; and
$R^{2A}$, $R^{3A}$ and $R^{4A}$ are as hereinbefore defined for formulae (IIA) and (IIB);
with a compound of formula (V):

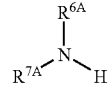
(V)

in which:
$R^{6A}$ and $R^{7A}$ are $R^6$ and $R^7$ as defined for formulae (IA) and (IB) or a group convertible to $R^6$ and $R^7$ respectively;
under amide forming conditions and thereafter, and if so needed;
converting P to hydrogen, and if necessary
converting an $R^{2A}$, $R^{3A}$, $R^{4A}$, $R^{6A}$ or $R^{7A}$ group to an $R^2$, $R^3$, $R^4$, $R^6$ or $R^7$ group;

(c) for a compound of formula (IA) in which $R^3$ and $R^4$ are both hydrogen and $R^1$ is $OR^5$, reacting an epi-mutilin compound of formula (IIC):

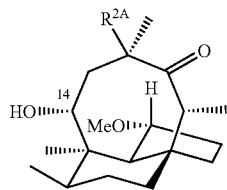
(IIC)

in which $R^{2A}$ is $R^2$ as defined for formulae (IA) and (IB), or a group convertible to $R^2$;
with a compound of formula (III) as hereinbefore defined; to give a compound of formula (VI):

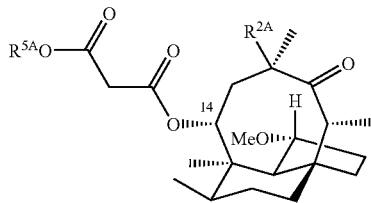
(VI)

and then treating the product with an acid;
and where required or desired converting an $OR^{5A}$ group to an $R^1$ group and an $R^{2A}$ group to an $R^2$ group; or (d) for a compound of formula (IA) in which $R^3$ and $R^4$ are both hydrogen and $R^1$ is $NR^6R^7$, reacting an epi-mutilin compound of formula (IVC):

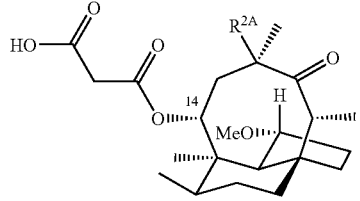
(IVC)

wherein $R^{2A}$ is as hereinbefore defined;
with a compound (V), as hereinbefore defined in an amide-forming reaction as hereinbefore described;
and then treating the product with an acid;
and where required or desired converting an $R^{2A}$ group to an $R^2$ group, an $R^{6A}$ group to an $R^6$ group
and an $R^{7A}$ group to an $R^7$ group.

\* \* \* \* \*